US007014638B2

(12) United States Patent
Michelson (10) Patent No.: US 7,014,638 B2
(45) Date of Patent: Mar. 21, 2006

(54) STAPLER HANDLE

(76) Inventor: Gary Karlin Michelson, 438 Sherman Canal, Venice, CA (US) 90291

( * ) Notice: Subject to any disclaimer, the term of this patent is extended or adjusted under 35 U.S.C. 154(b) by 0 days.

(21) Appl. No.: 10/647,933

(22) Filed: Aug. 26, 2003

(65) Prior Publication Data

US 2004/0035903 A1    Feb. 26, 2004

Related U.S. Application Data

(60) Division of application No. 09/618,197, filed on Jul. 18, 2000, now Pat. No. 6,609,322, which is a continuation of application No. 08/112,426, filed on Aug. 26, 1993, now Pat. No. 6,129,740, which is a continuation of application No. 07/692,583, filed on May 13, 1991, now abandoned, which is a continuation of application No. 07/341,848, filed on Apr. 24, 1989, now abandoned.

(51) Int. Cl.
*A61B 17/00* (2006.01)
*A61B 17/04* (2006.01)

(52) U.S. Cl. ........................... 606/1; 227/175.1
(58) Field of Classification Search ............... 601/40; 606/142, 1; 227/6
See application file for complete search history.

(56) References Cited

U.S. PATENT DOCUMENTS

| 156,431 A | 11/1874 | Luce |
| 547,447 A | 10/1895 | Paquot et al. |
| 1,028,032 A | 5/1912 | Krag |
| 1,202,707 A | 10/1916 | Grieco |
| 1,349,345 A | 8/1920 | Payne |
| D167,034 S | 6/1952 | Gottlieb et al. |
| 2,874,502 A | 2/1959 | Lockwood |
| 3,019,673 A | 2/1962 | Sjostkand et al. |
| 3,128,571 A | 4/1964 | Herrett |
| 3,167,876 A | 2/1965 | Milroy, Jr. |
| 3,661,187 A * | 5/1972 | Caveney et al. .......... 140/123.6 |
| 3,669,487 A * | 6/1972 | Roberts et al. ............. 294/104 |
| D230,974 S | 3/1974 | Howlett |
| 4,264,305 A * | 4/1981 | Rasmussen et al. .......... 433/90 |
| 4,330,093 A | 5/1982 | Chapman, Jr. |
| D272,278 S | 1/1984 | Green et al. |
| D277,029 S | 1/1985 | Blake, III et al. |
| 4,635,634 A * | 1/1987 | Santos ....................... 606/142 |

(Continued)

FOREIGN PATENT DOCUMENTS

| CH | 73402 | 10/1915 |
| DE | 2618074 | 11/1977 |
| FR | 550415 | 3/1923 |
| FR | 2845179 | 12/1981 |

OTHER PUBLICATIONS

English translation of Swiss Patent No. 73402 (J. Bocksberger and sons, Dec. 17, 1914).

(Continued)

*Primary Examiner*—Gary Jackson
(74) *Attorney, Agent, or Firm*—Martin & Ferraro, LLP (57) ABSTRACT

An ergonomic and proprioceptive handle design for instruments is disclosed. The handle can be used with a wide variety of medical instruments, such as a rongeur, as well as other instruments, such as guns and staplers.

16 Claims, 6 Drawing Sheets

U.S. PATENT DOCUMENTS

| | | | |
|---|---|---|---|
| 4,669,769 A | 6/1987 | Polder, Jr. | |
| 4,733,671 A | 3/1988 | Mehl | |
| 4,777,948 A | 10/1988 | Wright | |
| 4,962,747 A * | 10/1990 | Biller | 124/40 |
| 5,592,769 A | 1/1997 | Villani | |
| 5,768,817 A | 6/1998 | Simons | |

OTHER PUBLICATIONS

Electrical Construction & Maintenance, p. 151, Jan. 1978.

Industrial Design, p. 56, Sep. 1968.

Ramset catalog, Winchester Group, Olin Corp., Form B-552, 1969.

Remingotn Powder Actuated Fastening Systems, p. 5, Oct. 1974.

Mathews LTD, Olympic records held by VOSTOK, Sep. 1962, Shooting Times and Country Magazine, one page.

Colt Case, Guns and Ammo, Mar. 1976, Colt Case, pp. 74-75.

\* cited by examiner

STAPLER HANDLE

This is a divisional of application Ser. No. 09/618,197, filed Jul. 18, 2000 now U.S. Pat. No. 6,609,322, which is a continuation of application Ser. No. 08/112,426, filed Aug. 26, 1993, now U.S. Pat. No. 6,129,740, which is a continuation of application Ser. No. 07/692,583, filed May 13, 1991, now abandoned, which is a continuation of application Ser. No. 07/341,848, filed Apr. 24, 1989, now abandoned, all of which are incorporated herein by reference.

BACKGROUND

Hand powered instruments useful for biting tissues, known as rongeurs are common in the field of surgery. While there are many variations designed for use by one hand, the most common by far, would be the Pituitary, Kerrison, and Leksell types.

Prior hand operated rongeurs of the pituitary type have been characterized by a scissors like construction, with thumb and index finger grip holes, or of the Kerrison type using the thenar-palm line and four fingered handle. In these and other available designs, the forefinger is used to actuate the instrument from a position offset from the actuating operating mechanism so that the force required to close and open the instrument also translates in part into an upward displacement of the operating shaft and tip of the instrument. Not infrequently the surgeon finds it necessary to post the tip of the instrument into healthy tissue in order to limit the movement of the tip before biting or cutting the tissue to be removed. This injures healthy tissue. Also, due to the orientation of the hand and fingers, the location of the tip of the instrument is difficult to be mentally perceived, much less controlled, by the surgeon.

There is, therefore, a need for an improved handle for surgical instruments.

SUMMARY OF THE PRESENT INVENTION

The present invention consists of a rongeur having a main body portion which is the longitudinal proximal extension of the working shaft of the instrument. The most rearward portion of the body portion extends for approximately one inch over the dorsum of the hand, specifically in the notch formed by the junction of the thumb and index finger to the hand. Just distal to the proximate end of the body member, is the rear arcuate handle, the arc facing the rear end of the instrument. This rear handle is affixed to the body portion at essentially 90 degrees to the long axis of the body portion and will anatomically conform to the shape of the thenar eminence (the prominence of the muscles of the thumb) when the hand is in the "Bang Bang", "Fake Gun" or index finger pointing with the thumb extended position. In fact, the hand in grasping the instrument will, by means of said fixed proximal handle contour, be coaxed into assuming the desired position.

The lower portion of the rear handle continues, where it may either become convex or continue in line with the thenar portion, in which event said member would follow the shape of the thenar proximal, but would be more ulnar (towards the little finger side of the hand) such that in either case the ulnar border of the hand would be driven more proximal beneath the thenar's and with a tendency for the wrist, if unresisted, to assume a more extended (cocked-up) position. Spaced from the rear handle member of the instrument is a front downwardly disposed, pivotable arcuate handle member, of a length sufficient to accommodate the long, ring and little fingers of the hand. The lower portion of the front handle may be curved to facilitate finger placement and provide for a cradling of the lowest finger, thereby providing for a better feel and more control. A spring mechanism associated with the front handle, is utilized to urge the front handle to its original forward position. In alternative embodiments, the front handle may be fixed and provided with a trigger housing and mechanism for activating the rongeur. For example, if the rongeur is electrically powered, the trigger within the housing would activate the rongeur.

The instrument of the present invention is grasped quite differently from all other prior surgical instruments in that the index finger is separated from the remaining three fingers and is left extended along the main shaft of the instrument, pointing, while the three remaining fingers are wrapped around the unusually short front handle or trigger. The thumb is fully extended and may come to rest in more distal position, relative to its natural resting position and to the other fingers of the hand, as the shape of the rear handle urges the thumb portion of the hand forward and the wrist into a more extended (cocked-up) position. The part of the body portion coming to lie between the thumb and index fingers, which are relatively opposed, is called the "pinch pad" area of the body portion of the instrument.

The following advantages of the present invention are a product of the handle design and the induced finger, hand, and wrist positions:

1. Ambidextrous.
2. Anatomic to the working position profile of the inside of the partially closed hand.
3. Anatomic to and thus induces the optimal functional finger, hand and wrist positions.
4. Recruits the "Automatic Hand Effect" to optimize the instrument function. If no attempt is made to inhibit it, it can be observed that taking the fingers from the fully extended position with the hand straight out to the semi-closed finger grasping position, causes the wrist to go into the "cocked-up" position automatically. This effect is deliberately elicited by the handle design and is beneficial in at least two ways. Firstly, it allows for the proper alignment, discussed below, and secondly it improves the finger flexion function, as described below in Item 6.
5. While the handle design deliberately elicits the described wrist extension, this in fact results in the absolute longitudinal alignment of the surgical instrument through the hand and wrist with the forearm.
6. Finger flexion. The means of operating these instruments is facilitated by wrist extension. This is easily proven by assuming the opposite position and attempting to make a fist with the wrist fully flexed.
7. Elimination of the operating shaft/hand vertical displacement, increasing control.
8. Maximalization of hand contact is achieved for added control. The thumb and index fingers contact the body portion throughout their entire length. The palm engages the handle across its entire breadth, with the thenar engaging and almost encircling the rear handle portion. The three remaining fingers literally wrap around the front handle portion.
9. Minimalization of skin contact pressures.
10. Fits all size hands, because the lower three fingers wrap the pivotal front handle or trigger, and since it does not matter whether it is more proximally or distally, the handle will function well, and feel good to hands of all sizes.
11. Increased mechanism capacitance of springs and the like in the body portion.

12. The surgeon's hand is not exposed to any sharp or moving parts.

13. Enhanced instrument stability. The opposition of the thumb and index fingers on either side of the "pinch pad" stabilizes the instrument against side to side movement, while the instrument is also stabilized against any up and down movement by both the rear and front handles, which have both upper and lower contoured stops.

14. Ergonomic. The handle is biomechanically engineered to facilitate the human hand function in its operation.

15. Proprioceptive. Proprioception or kinesthetic sense is the ability to correctly spacially locate a bodily part without the use of vision. This allows one to easily place a finger in the ear or on the tip of the nose, even with the eyes closed. The index finger first, and the tactile pulp of the thumb secondly, are the most richly invested with this kinesthetic capacity. Prior rongeurs have failed to take advantage of this, and have allowed both the index finger and thumb to face away from the intended target, or to be curled up in and upon themselves. The present design aligns the index finger and thumb along the longitudinal axis of the instrument such that they always point exactly at the target, and thereby facilitate the accurate placement of the instrument by the operator, without the need to visually monitor that action. This is extremely important as it allows the surgeon to remain focused at the surgical site even as the instrument is passed into and away from that site, and without the need for the surgeon to perform continuing and repetitive disruptive reorientations.

16. The absence of reactive tip excursion. Since the typical rongeur provides for only two points of hand fixation to the handle, when an attempt is made to operate the instrument by imparting of force at the handle, there is an excursion of the tip, according to Newton's 3rd law of action and equal reaction, such that the tip is moved from the intended targeted tissue. With the present invention, stabilization of the instrument distal to the application of the trigger force, at the "pinch pad", allows for the requisite reactionary counter force required to neutralize the proximal force, thereby leaving the tip free of any undesirable excursion during the instrument's operation.

17. The design is compact and requires reduced operating space because of the absence of any vertical displacement of the grasped area from the instrument shaft axis and by aligning the instrument axis and containing the entire handle within the hand. As a direct result, smaller incisions and less wound retraction is required for the operation of instruments with handles so designed.

18. Ultra-low profile.

19. Enhanced sight visualization as the view of the tip is unobstructed by any protrusions.

20. Line of sight targeting. The instrument design facilitates the accurate aiming of the instrument, much like sighting a rifle. The extended index finger and aligned instrument shaft are like the rifle barrel, while the instrument tip is the front bead, and the anatomical "V" of the thumb and index finger, bisected by the proximate handle extension, is the rear targeting site.

21. Universality. This handle's design can be utilized for a large variety of previously disparate rongeur types, thereby facilitating surgery, in that each instrument feels and operates in the identical fashion.

22. Increased comfort.

23. Increased maneuverability.

24. A stronger and more rigid instrument. The overall length of the instrument and displacement of the handle from the axis of the instrument are minimized by aligning the instrument within the hand and containing the handle therein. Reduction of the instrument length and the displacement of the points of application of force to the extended lever arm results in a more rigid and stronger construct.

25. More durable.

OBJECTS OF THE PRESENT INVENTION

It is therefore an object of the present invention to provide an improved handle for a medical instrument that is ergonomic;

It is another object of the present invention to provide an improved handle for a medical instrument that is easier to use;

It is another object of the present invention to provide an improved handle for a medical instrument that automatically correctly positions the hand of the user on the instrument;

It is another object of the present invention to provide an improved handle for a medical instrument that is more comfortable and causes less fatigue during use;

It is another object of the present invention to provide an improved handle for a medical instrument that is more durable;

It is another object of the present invention to provide an improved handle for a medical instrument provides for improved proprioception of the instrument tip;

It is still another object of the present invention to provide an improved handle for a medical instrument that is more stable.

These and other objects of the present invention will be apparent from a review of the following specification and the accompanying drawings.

BRIEF DESCRIPTION OF THE DRAWINGS

FIG. 5 also illustrates that the instrument is ambidextrous.

DETAILED DESCRIPTION OF THE DRAWINGS

Referring to FIGS. 1–5, there is shown a first embodiment of a surgical-instrument 10 constructed in accordance with the present invention. The instrument 10 is a hand operated rongeur having a body portion 12 with a depending rear handle 20 and front handle 22. The cross section of the body portion 12 is generally rectangular. A working shaft 16 extends distally from the body which terminates in a rongeur biting mechanism 18 of conventional construction. The rear handle 20 is fixed. The forward handle 22 is connected to operating mechanisms contained within the body portion 12 and is pivoted about a pivot pin 24 or other means for movement to actuate the biting mechanism in response to a squeezing movement of the surgeon's hand.

Figure 1:
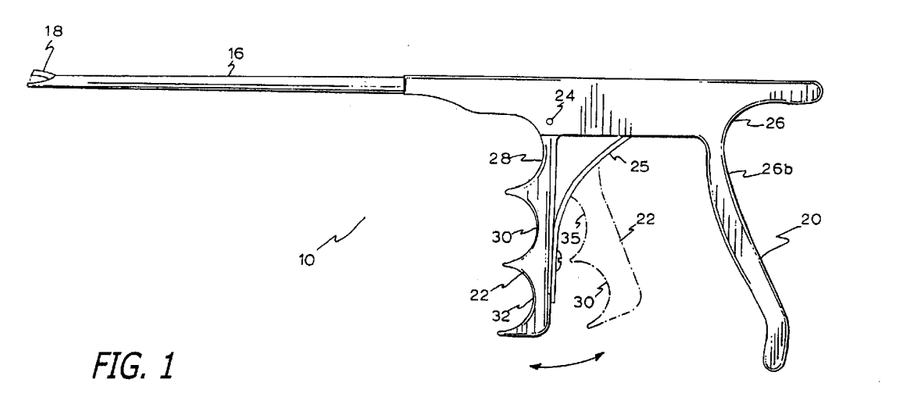
FIG. 1 is a side elevational view of a surgical instrument constructed in accordance with the present invention.

The body portion 12 has a proximal extension 14 at its rear end which joins the rear handle 20 to form a rearwardly facing continuous curved portion 26. The proximal extension 14 extends for approximately one inch over the dorsum of the hand, specifically in the notch formed by the junction of the thumb and index finger.

The body portion 12 in line with the longitudinal axis of the working shaft 16 of the instrument 10, has a width which, in the preferred embodiment, is approximately 8 mm. The body portion 12 has a length in the preferred embodiment of 9 cm. The shaft of the instrument is, approximately 15 cm. Thus the instrument 10 has an overall length of about 24 cm.

The rear handle 20 extends substantially at right angles to the body portion 12 and is in the shape of a rearwardly facing thenar fitting curve 26b formed to lie comfortably in the hand, cradled along the thenar-palm of the hand such that the palm closely fits up to the instrument with the thumb and forefinger naturally extending on both sides of the body portion 12, each projecting distally along a respective side at the top of the body portion 12. The rear handle 22 anatomically conforms to the shape of the thenar eminence (the prominence of the muscles of the thumb) when the hand is in the make-believe gun of childs play position with the index finger pointing and the thumb in an extended position. In fact, the hand, in grasping the instrument, will, by means of the fixed rear handle contour, be coaxed into assuming the described position.

The portion of the rear handle 20 below of the thenar cradle portion, continues where it may form a reverse curvature to become convex or continue in line with the thenar portion such that the ulnar border of the hand is driven to a more proximal position beneath the thenar's and with a tenancy for the wrist to assume a more extended or cocked-up position.

Figures 2, 4:
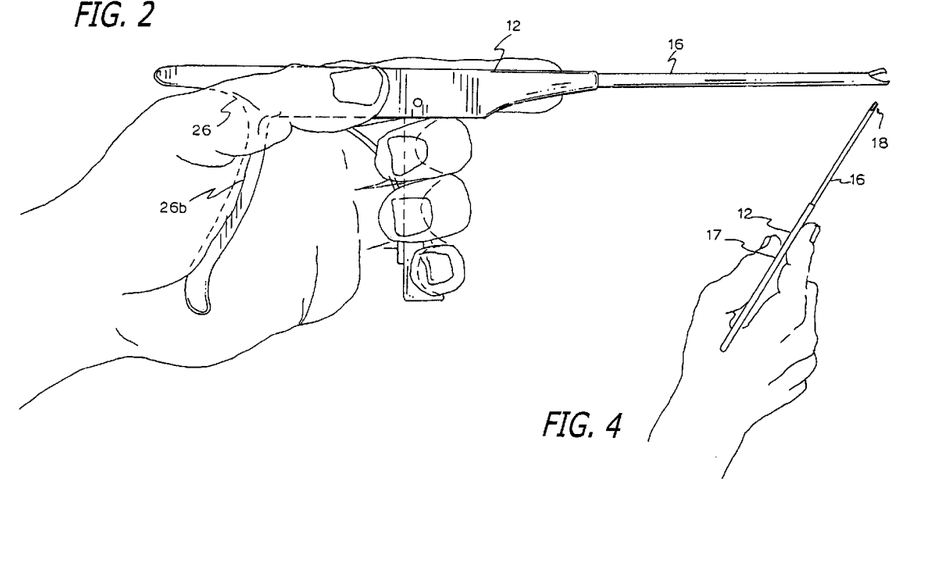
FIG. 2 is a side view of the instrument of FIG. 1 being held in the hand.
FIG. 4 is a top perspective view of the surgical instrument held in the hand.
Figure 3:
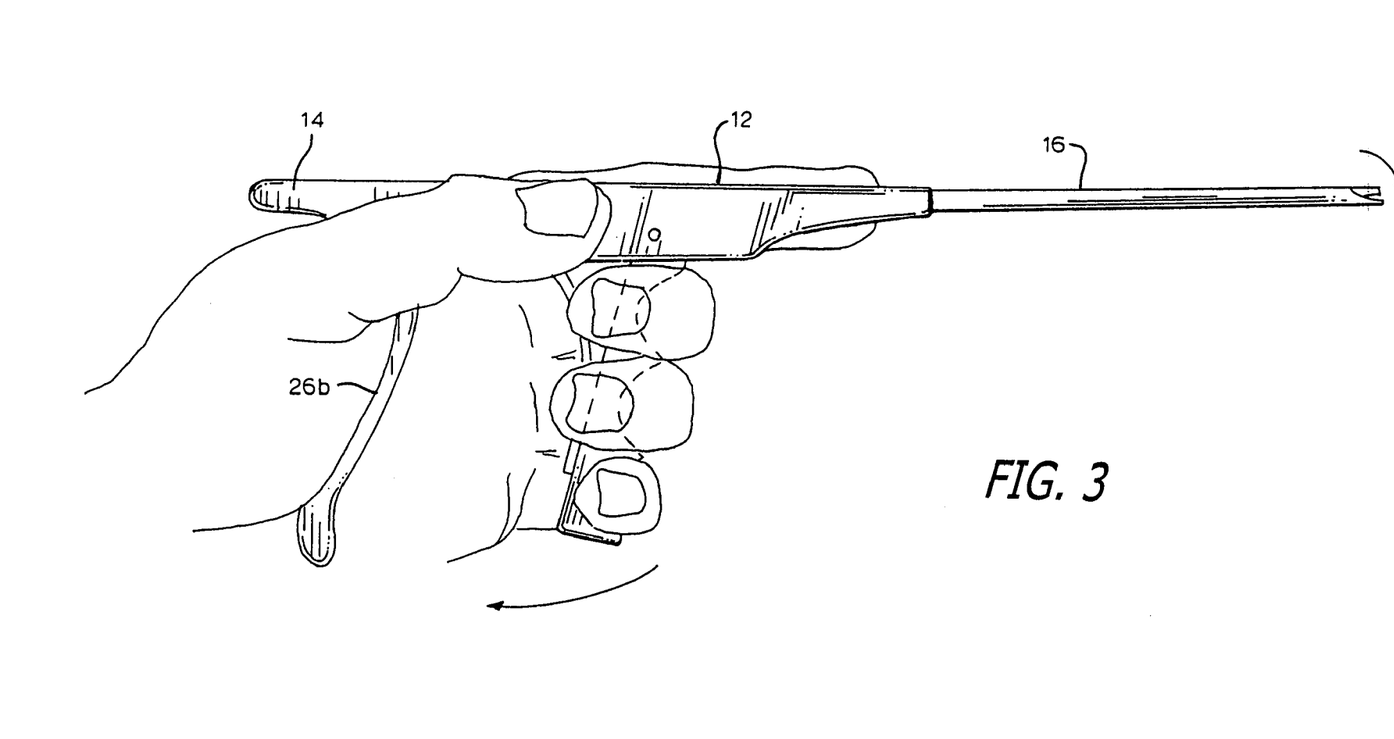
FIG. 3 is a side view of the surgical instrument of FIG. 1 as held in the hand of a surgeon in the retracted position.
Figure 5:
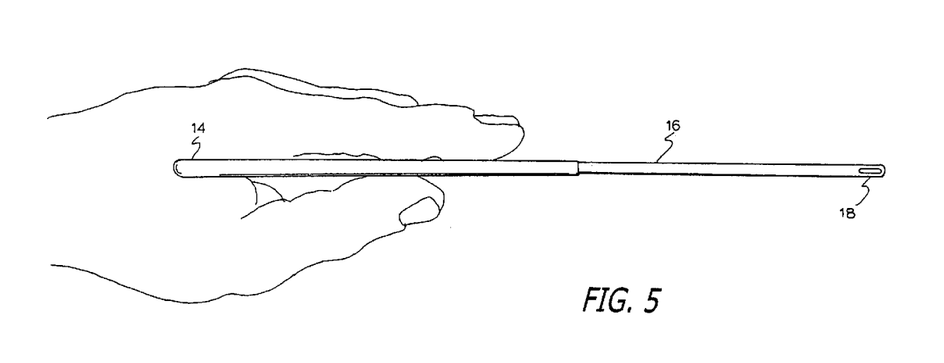
FIG. 5 is a top view of the instrument to the surgeon as viewed by him.

The front handle 22 is shaped for gripping by the remaining three fingers and for actuating the instrument. The front handle 22 is connected to the body portion 12 by pivot pin 24 or other means, at a position spaced forwardly from the rear handle 20 at a distance about equal to that distance between the joint of the thumb and the forefinger to the first finger joint of the middle finger. The portion of the body 12 where the thumb and index finger grasps the body portion is the pinch pad 17, as shown in FIG. 4. A portion 23 of the front handle further extends within the body portion 12 so that when the front handle 22 or trigger is pulled proximally about pivot pin 24, the jaws 18 of the biting instrument close. Though a push mechanism is described, pull and other mechanisms may be employed with the present invention as would be evident to those familiar with the art of fabricating surgical instruments.

The front handle 22 extends downwardly to accommodate the width of three fingers, so that as the instrument 10 is held, it is natural to extend the thumb and forefinger along the top of the body 12 directly in line with the working shaft 16 and to wrap the remaining fingers about the front handle. Indentations 28, 30 and 32 provide placement of these fingers.

A spring mechanism 34, or any other internal, external, or combination thereof, is utilized to urge the pivotable front handle 22 or trigger to its normal position.

The instrument is grasped quite differently from other surgical instruments, in that the index finger is separated from the remaining three fingers and is forced to extend along the main member of the body of the handle, while the three remaining fingers are wrapped around the shorter front handle, which serves in the embodiments shown as the trigger.

Thus, the fingers of the hand do not engage the rear handle 20, contrary to the conventional instruments. Also, the index finger and the thumb of the surgeon do not engage the front handle, but come to rest on the pinch pad 17, a position which permits and promotes the advantages set forth above. Note that the portion of the hand, as shown in FIGS. 2–5, is below the plane of the top surface of the instrument and the handle.

While the present invention has been described in terms of the preferred embodiment in association for use with a rongeur, it may be used with other instruments, including, but not limited, scissors or the like, guns or staplers. Also, it is recognized that the size of the instrument can be varied, without departing from the present inventive concept.

Figure 6:
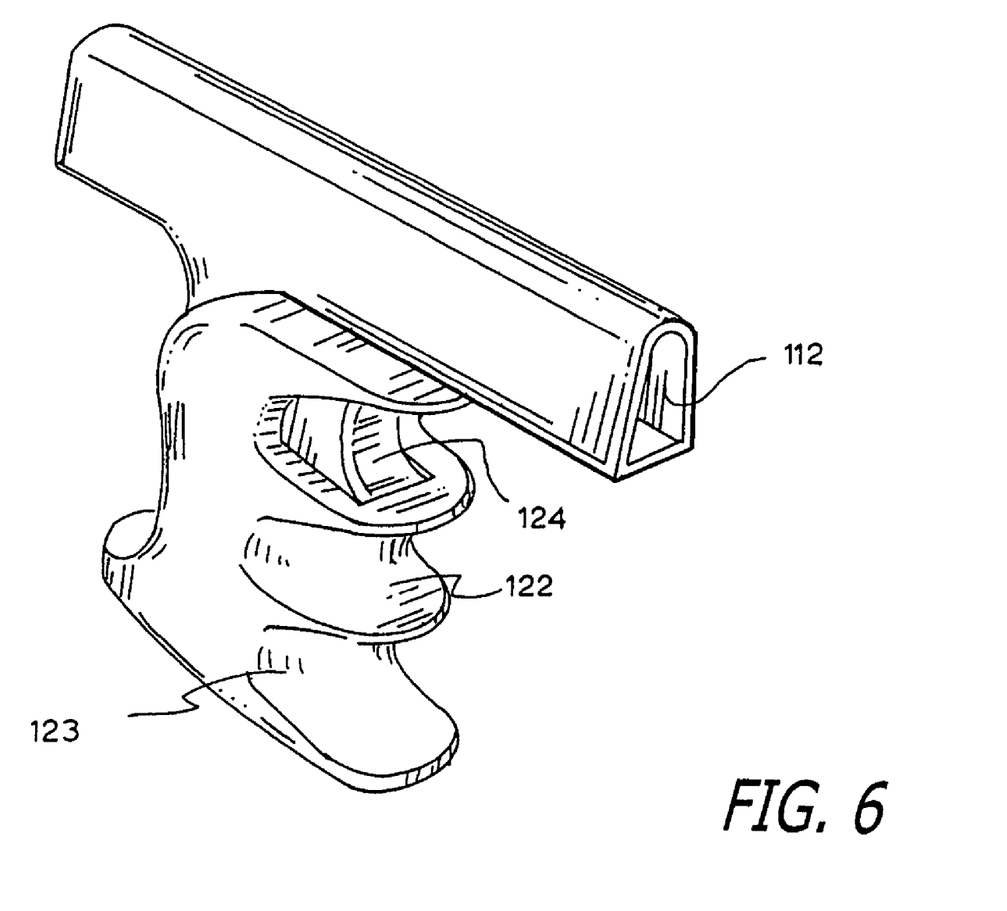
FIGS. 6-8 are perspective views an alternative embodiment of the invention.
Figures 7, 8:
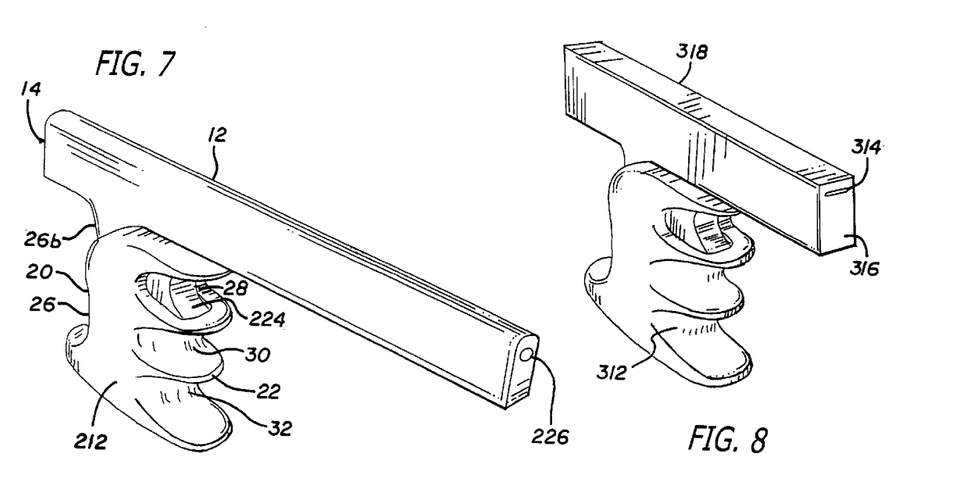

Referring to FIGS. 6–8. alternative embodiments of the present invention are shown, in which the handle is in the form of a gun butt, with a separate trigger mechanism.

In FIG. 6 the handle 110 has a replaceable instrument receiving housing 112 for permitting interchangable instrument tips to be used with the basic handle design. The front handle 122 receives the lower three fingers of the hand, and has a trigger 124 for activating the mechanism.

In FIG. 7, the handle 212 is shown for use with a gun. the trigger 224 is activated by the middle finger, with the thumb and fore finger pinching the barrel 226 of the gun.

In FIG. 8, the handle 312 is used for a stapler. The staples would be ejected from the opening 314 in the from face 316 of the staple storage compartment 318.

I claim:

1. A stapler comprising:
   a body having a longitudinal axis, a rear, and a front axially aligned with the longitudinal axis of said body, said body including a staple storage compartment;
   a handle depending downwardly from said body, said handle having a thenar fitting concave curve adapted to conform to the natural curvature of the thenar eminence of the palm of a user's hand and facing said rear of said body and a proximal extension extending rearwardly proximate the juncture of said body and said handle, said proximal extension adapted to extend over the dorsum of the user's hand and having a bottom surface adapted to contact the top of the doreum, said body having at least a pair of sides at least in part parallel to the longitudinal axis of said body forming a grasping area for the thumb and the index finger of the user's hand, said grasping area adapted to permit the placement of the thumb and the index finger to the user's hand on said grasping area generally parallel to and facing one another and generally in line with the longitudinal axis of said body, whereby when the user's hand is placed on said handle, the dorsum is in contact with said bottom surface of said proximal extension, the thenar eminence is in contact will, said thenar fitting concave curve, and the index finger and the thumb of the user's hand are placed adjacent to said body and parallel to the longitudinal axis of said body; and
   a mechanism for ejecting staples from said staple storage compartment.

2. The stapler of claim 1, wherein said handle has recessed portions for receiving the lower fingers of the user's hand.

3. The stapler of claim 1, wherein the lower portion of said handle has a second concave curve with a concavity facing said body of said stapler.

4. The stapler of claim 1, wherein said body comprises a stapler ejection opening across the front of said body.

5. The stapler of claim 1, wherein said proximal extension extends at least one inch over the dorsum of the user's hand.

6. The stapler of claim 1, wherein said mechanism comprising a trigger.

7. The stapler of claim 1, wherein said handle includes a plurality of indentations adapted to accommodate fingers other than the thumb and index finger when said stapler is being grasped by the user's hand.

8. The stapler of claim 7, wherein said handle includes three indentations adapted to separate three fingers from each other while said stapler is being grasped by the user.

9. The stapler of claim 7, wherein said handle includes a trigger at least in part within one of the indentations.

10. The stapler of claim 9, wherein the exposed surface of said trigger is within the confines of one of the indentations.

11. The stapler of claim 1, wherein said handle is adapted to accommodate at least two fingers of a user and including a trigger adapted to be actuated by a user's middle finger.

12. The stapler of claim 1, wherein the staple storage compartment is axially aligned with the longitudinal axis of said body.

13. The stapler of claim 1, further comprising an opening located on said front of said body for permitting staples to exit said staple storage compartment.

14. The stapler of claim 13, wherein said opening is a slot.

15. A method for grasping a stapler having a body with a longitudinal axis, a concave thenar fitting rear handle depending from the body, a storage compartment extending from the body generally along the longitudinal axis of the body, the body having a grasping area for the thumb and the index finger of a user's hand, a proximal extension extending rearwardly proximate the juncture of the body and the handle, the proximal extension having a bottom surface adapted to contact the top of the dorsum of the user's hand, said method comprising the steps of:

placing the handle of the stapler in the palm of the user's hand with the thenar eminence of the palm in contact with the concave thenar fitting handle;

placing the dorsum of the user's hand in contact with the bottom surface of the proximal extension;

positioning the index finger and the thumb opposing one another along the body of the stapler; and placing the three remaining fingers of the user's hand around the handle of the stapler.

16. The method of claim 15, wherein the positioning step includes the sub-step of aligning the index finger and the thumb opposing one another along the body of the stapler at the grasping area such that the index finger and the thumb point at the intended target of said stapler.

* * * * *

UNITED STATES PATENT AND TRADEMARK OFFICE
CERTIFICATE OF CORRECTION

PATENT NO. : 7,014,638 B2
DATED : March 21, 2006
INVENTOR(S) : Gary Karlin Michelson It is certified that error appears in the above-identified patent and that said Letters Patent is hereby corrected as shown below:

Column 6,
Line 40, change "doreum" to -- dorsum --;
Line 45, change "to" to -- of --;
Line 51, change "will," to -- with --; and
Line 67, change "prising" to -- prises --.

Signed and Sealed this

Ninth Day of May, 2006

JON W. DUDAS
*Director of the United States Patent and Trademark Office*